US007943648B2

(12) United States Patent
Guo et al.

(10) Patent No.: US 7,943,648 B2
(45) Date of Patent: *May 17, 2011

(54) SALTS OF IMIDAZOLE-5-CARBOXYLIC ACID DERIVATIVES, A METHOD FOR PREPARING SAME AND PHARMACEUTICAL COMPOSITIONS COMPRISING SAME

(75) Inventors: Jianghui Guo, Shanghai (CN); Dong An, Shanghai (CN)

(73) Assignee: Shanghai Allist Pharmaceutical Inc., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/478,954

(22) Filed: Jun. 5, 2009

(65) Prior Publication Data

US 2009/0326024 A1 Dec. 31, 2009

Related U.S. Application Data

(63) Continuation of application No. PCT/CN2006/003301, filed on Dec. 6, 2006.

(51) Int. Cl.
*A61K 31/41* (2006.01)
*C07D 257/04* (2006.01)

(52) U.S. Cl. ...... 514/381; 514/383; 548/253; 548/262.2

(58) Field of Classification Search ................ 514/381, 514/383; 548/253, 262.2
See application file for complete search history.

(56) References Cited

U.S. PATENT DOCUMENTS

| 5,138,069 A | 8/1992 | Carini et al. |
| 5,196,444 A | 3/1993 | Naka et al. |
| 5,298,519 A * | 3/1994 | Binder et al. .................. 514/381 |
| 5,616,599 A | 4/1997 | Yanagisawa et al. |
| 2009/0036505 A1* | 2/2009 | Guo et al. ...................... 514/381 |

FOREIGN PATENT DOCUMENTS

| CN | 1071426 | 4/1993 |
| EP | 0 253 310 | 1/1998 |
| WO | 2005/011646 | 2/2005 |
| WO | 2005/023182 | 3/2005 |
| WO | 2006/115187 | 11/2006 |
| WO | WO 2007/095789 | 8/2007 |

OTHER PUBLICATIONS

International Search Report of PCT/CN2006/003301, dated Jun. 28, 2007.
Mealy et al., "Elisartan Potassium. Antihypertensive Angiotensin II Antagonist." Drugs of the Future, vol. 21, No. 2, 1996, pp. 139-142.

* cited by examiner

*Primary Examiner* — Susannah Chung
(74) *Attorney, Agent, or Firm* — Hamre, Schumann, Mueller & Larson, P.C.

(57) ABSTRACT

The present invention provides pharmaceutically acceptable salts of imidazole-5-carboxylic acid derivatives, methods for preparing same and pharmaceutical compositions comprising same. The salts obtained by the present invention can be easily dissolved in common solvents, such as water and methanol. The bioavailability thereof is good in animal body. Thereby it is applicable to be developed as a normal preparation for treating hypertension.

7 Claims, No Drawings

SALTS OF IMIDAZOLE-5-CARBOXYLIC ACID DERIVATIVES, A METHOD FOR PREPARING SAME AND PHARMACEUTICAL COMPOSITIONS COMPRISING SAME

CROSS-REFERENCE TO RELATED APPLICATIONS

This application is a continuation of and claims priority to International Application No. PCT/CN2006/003301 filed on Dec. 6, 2006, the contents of which are incorporated herein in their entirety by reference.

TECHNICAL FIELD

The present invention relates to pharmaceutically acceptable salts of imidazole-5-carboxylic acid derivatives, a method for preparing same and pharmaceutical compositions comprising same. The new forms of these compounds are synthesized by studying on methods of the salt formation of imidazole-5-carboxylic acid derivatives, which effectively resolved the complex problems in preparation technology resulted from the bad solubility of this kind of compounds.

BACKGROUND OF THE INVENTION

Angiotensin II, a main vasoconstrictor hormone of renin-angiotension-aldosterone system (RAAS), plays an important role in pathological physiology of many chronic diseases. The production approach of Angiotensin II which is present in various tissues is mainly as follows: angiotensinogen acted on by renin can be converted to angiotensin I (Ang I) of decapeptide which only has a little activity in contraction of blood vessel; and can be further converted by angiotensin converting enzyme to angiotensin II (Ang II) of octapeptide which is the final physiological active substance of renin-angiotension-aldosterone system (RAS) and can induce physiological functions such as contraction of blood vessel and elevation of blood pressure by binding to specific angiotensin II (ATII) receptor.

EP0253310 discloses a series of imidazole derivatives. It has been found by E. I. Du Pont de Nemours and Company (US) through researches that a compound coded DUP753 has a good effect on lowering blood pressure. It was approved in 1994 and became the first non-peptide type Ang II receptor antagonist, i.e. losartan potassium, which inhibits contraction of blood vessel by selectively blocking the actions of angiotensin II of smooth muscle in blood vessel on its Ang I receptor to achieve the functions of dilating blood vessel and reducing blood pressure.

With development and marketing of losartan potassium, various medical R&D organizations and companies began to study successively on structure of Ang II receptor antagonists. U.S. Pat. No. 5,196,444 discloses a series of benzimidazole derivatives and preparation processes therefor. Such derivatives have angiotensin II antagonistic activity and antihypertensive activity and thereby can be used to treat hypertensive diseases. Among them, candesartan was developed and marketed in 1997 by Takeda Chemical Industries, Ltd. (JP), which releases ester group in vivo and is hydrolyzed to its active metabolite to act on lowering blood pressure.

U.S. Pat. No. 5,616,599 discloses a series of 1-biphenylmethylimidazole derivatives whose structures are similar to that of losartan. The significant difference in structures therebetween is that the chlorine atom at the 4-position of the imidazole ring of losartan is converted to 1-hydroxy-1-methyl-ethyl and the 5-position thereof is converted to a carboxy group, hydroxy group or pro-drug structures such as esters or amides. It is demonstrated to have good activity in lowering blood pressure. Therefore, Sankyo Company, Ltd. (JP) developed and marketed a drug of olmesartan.

PCT/CN2006/001914 described a series of imidazole-5-carboxylic acid derivatives. The characteristic in its structure is that the 5-position of the imidazole ring is converted to an acylal group. This kind of compounds show good activity in lowering blood pressure in animals. Compared with other Ang II receptor antagonists, these imidazole-5-carboxylic acid derivatives have lower toxicity.

However, through studying on a series of imidazole-5-carboxylic acid derivatives, they were found to be hardly dissolved in conventional solvents. Pharmaceutical methods, such as solid dispersion technology, were used to increase the water solubility thereof, which lead to the complexity of preparation technology. Therefore, in order to explore more ideal antihypertensive drugs, there is an urgent need to develop a new form of imidazole-5-carboxylic acid derivatives with good solubility, and applicability for normal preparation technology.

CONTENTS OF INVENTION

The present invention provides a series of pharmaceutically acceptable salts of imidazole-5-carboxylic acid derivatives, methods for preparing same and pharmaceutical compositions comprising same.

In the first aspect, the present invention provides a series of pharmaceutically acceptable salts of imidazole-5-carboxylic acid derivatives of the formula (I)

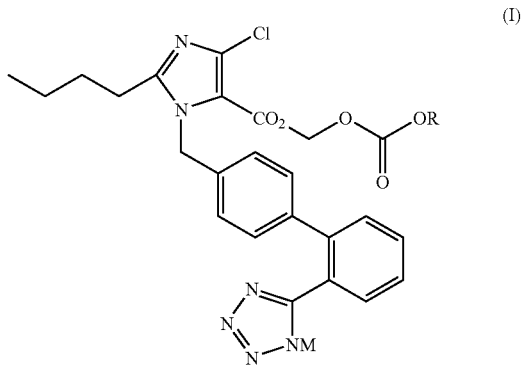

wherein R is selected from the group consisting of hydrogen, straight or branched $C_1$-$C_4$ alkyl, or $C_3$-$C_7$ cycloalkyl, wherein said alkyl or cycloalkyl group is unsubstituted or substituted by 1-3 substituents selected from the group consisting of F, Cl, Br, and OH;

M is a metal ion or ammonium ion.

In a preferred embodiment of the present invention, R is selected from the group consisting of straight or branched $C_2$-$C_4$ alkyl.

In another preferred embodiment of the present invention, R is selected from the group consisting of ethyl, isopropyl or tertiary butyl.

In another preferred embodiment of the present invention, R is isopropyl.

In a further preferred embodiment of the present invention, the salts are selected from the group consisting of alkali metal salts and alkaline earth salts, especially potassium salts, sodium salts or calcium salts.

In the second aspect, the present invention provides a method for preparing pharmaceutically acceptable salts of formula (I) comprising the following step:
(a) In an inert organic solvent, compounds of formula (II) are reacted with reagents which can provide a metal ion or ammonium ion to form salts of formula (I),

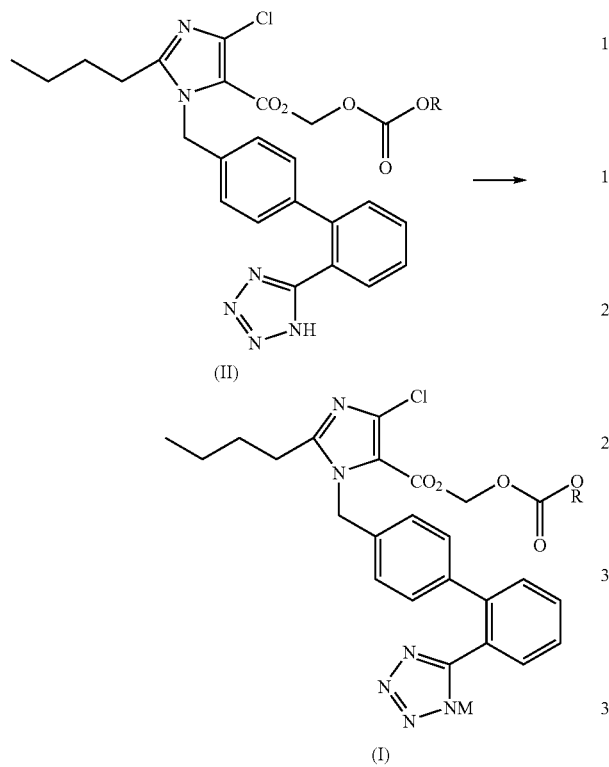

wherein R is selected from the group consisting of hydrogen, straight or branched $C_1$-$C_4$ alkyl, or $C_3$-$C_7$ cycloalkyl, wherein said alkyl or cycloalkyl group is unsubstituted or substituted by 1-3 substituents selected from the group consisting of F, Cl, Br, and OH;

M is a metal ion or ammonium ion.

In a preferred embodiment of the present invention, the preparation method further comprises a step as follows:

(b) The salt of formula (I) is isolated from the mixture of the reaction.

It is preferred that in step (b) the solid product is obtained by isolating from the reaction solution directly or obtained by recrystallization from the crude solid product by concentration in vacuo.

In another preferred embodiment of the present invention, the metal ions are selected from the group consisting of alkali metal ions and alkaline earth ions.

In a further preferred embodiment of the present invention, the reagents can provide metal ions are selected from the group consisting of trimethyl silicates, 2-ethyl-hexanoates, carbonates or metal chlorides.

In the third aspect, the present invention provides a pharmaceutical composition comprising the pharmaceutically acceptable salts of the formula (I), and pharmaceutically acceptable carriers.

In the fourth aspect, the present invention provides a use of pharmaceutically acceptable salts of the formula (I) in the preparation of antihypertensive drugs.

In the fifth aspect, the present invention provides a treatment method of diseases, which can be alleviated or treated by inhibiting the receptor I of angiotensin II (Ang II). The method comprises the follows steps: the patients to be treated take 0.05~30 mg/kg body weight/day pharmaceutically acceptable salts of the formula (I).

In a preferred embodiment of the present invention, the salts are selected from the group consisting of alkali metal salts and alkaline earth salts.

In another preferred embodiment of the present invention, the disease is hypertension.

THE EMBODIMENTS OF THE PRESENT INVENTION

After intensive and extensive study, the inventors of the present invention have discovered that the solubility of some salts of imidazole-5-carboxylic acid derivatives, especially the alkali metal salts and alkaline earth salts thereof, is very good. The present invention has been completed based on this discovery.

Pharmaceutically Acceptable Salts

In the present invention, "the compounds of the present invention" can be exchanged with "the salts of the present invention", they both refer to the pharmaceutically acceptable salts of formula (I) obtained from the compounds of formula (II), especially the alkali metal salts and alkaline earth salts thereof. The specific compounds of the present invention are pharmaceutically acceptable salts of imidazole-5-carboxylic acid derivatives of formula (I):

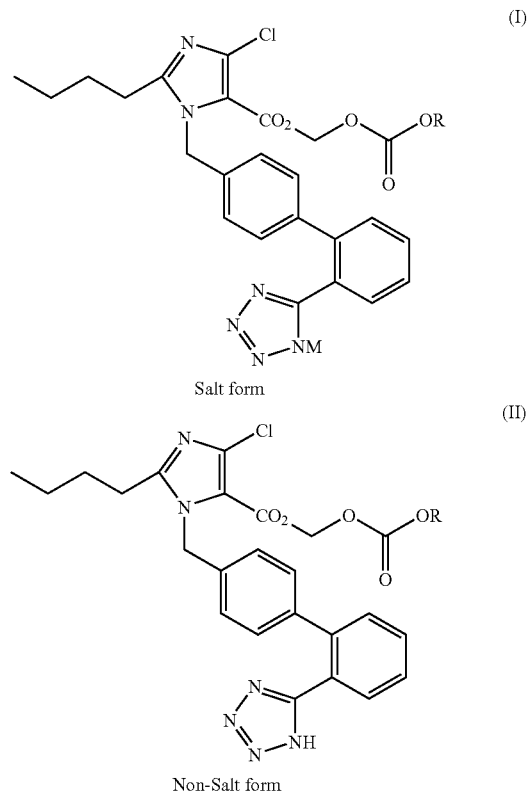

wherein R is selected from the group consisting of hydrogen, straight or branched $C_1$-$C_4$ alkyl, or $C_3$-$C_7$ cycloalkyl, wherein said alkyl or cycloalkyl group is unsubstituted or substituted by 1-3 substituents selected from the group consisting of F, Cl, Br, and OH;

M is a metal ion or ammonium ion.

In a preferred embodiment of the present invention, R is selected from the group consisting of straight or branched $C_2$-$C_4$ alkyl, preferably, ethyl, isopropyl or tertiary butyl.

In the present invention, the especially preferred compounds are pharmaceutically acceptable salts of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester (R=isopropyl).

In the present invention, the pharmaceutically acceptable salts are relatively nontoxic salts, preferably the alkali metal salts and alkaline earth salts of imidazole-5-carboxylic acid derivatives, such as potassium salts, sodium salts, lithium salts, magnesium salts, calcium salts or zinc salts, more preferably potassium salts, sodium salts or calcium salts.

The especially preferred pharmaceutically acceptable salts are potassium salts, sodium salts or calcium salts of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester.

The Preparation Process

The present invention also provides a process for preparing the pharmaceutically acceptable salts of imidazole-5-carboxylic acid derivatives of formula I, which includes the following step:

(a) In an inert organic solvent, the compounds of formula (II) are reacted with reagents which can provide a metal ion to form salts of formula (I), such as alkali metal salts or alkaline earth salts thereof.

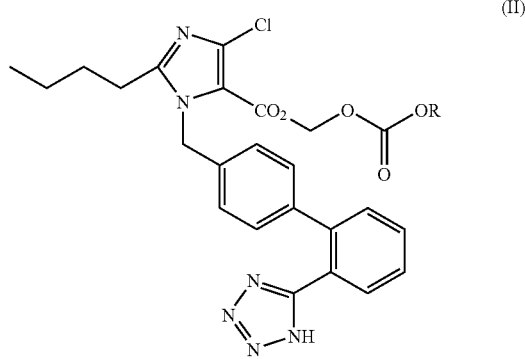

(II)

In a specific embodiment, this process includes the steps as follows:

(i). In an organic solvent, 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester is reacted with reagent which can provide a metal ion.

(ii). The solid salt of formula (I) is obtained by being isolated from the reaction solution directly or the crude solid product is obtained by being concentrated in vacuo.

(iii). The target product is obtained by recrystallization in organic solvents.

The reagents which can provide a metal ion or ammonium ion used in the process of the present invention include organic acid salts, organic bases, inorganic bases or metal chlorides etc.

The organic acid salts include dodecyl phosphates, hexadecyl phosphates, acetates or 2-ethyl hexanoates etc., such as sodium dodecyl phosphate, potassium dodecyl phosphate, sodium hexadecyl phosphate, potassium hexadecyl phosphate, sodium acetate, potassium acetate, sodium 2-ethyl hexanoate or potassium 2-ethyl hexanoate.

The organic bases include: sodium methylate, potassium methylate, sodium ethylate, potassium ethylate, sodium methyl mercaptide, potassium methyl mercaptide, sodium methyl silanolate, potassium methyl silanolate, sodium trimethyl silanolate or potassium trimethyl silanolate.

The inorganic bases include: potassium carbonate, sodium carbonate, magnesium carbonate, zinc carbonate, lithium carbonate, calcium carbonate, potassium bicarbonate, sodium bicarbonate, magnesium bicarbonate, zinc bicarbonate, lithium bicarbonate, potassium hydroxide, sodium hydroxide, calcium hydroxide or magnesium hydroxide.

The metal chlorides include: calcium chloride, potassium chloride, magnesium chloride or zinc chloride.

Generally, the preparation process mentioned above is a temperature controlled reaction. The selection of reaction temperature will influence the reaction for forming salts. The temperature of reaction is 0~80° C., preferably 0~50° C.

After the reaction being finished, the compounds of the present invention can be isolated or purified by conventional methods. For example, the solid product can be precipitated directly, or the solid product can be obtained by concentrating the reaction solution in vacuo. The crude product is washed by a little ethyl acetate, then undergo a recrystallization in organic solvents to form the salts of the present invention.

Pharmaceutical Composition and Use

The compounds of the present invention can be administered to human orally, rectally, parenterally (intravenously, intramuscularly or subcutaneously), locally. Said compounds can be administered alone or in combination with other pharmaceutically acceptable compounds. It should be noted that the compounds according to the present invention can be administered as a mixture.

Solid dosage forms for oral administration include capsules, tablets, pills, powders and granules. In such solid dosage forms, the active compound may be mixed with at least one conventional inert excipients (or carriers) such as citrate sodium or dicalcium phosphate, or mixed with the following components: (a) fillers or compatibilizers, for example, starch, lactose, sucrose, glucose, mannitol and silicic acid; (b) binders, for example, hydroxymethylcellulose, alginate, gelatin, polyvinylpyrrolidone, sucrose, and arabic gum; (c) humectants, for example, glycerin; (d) disintegrants, for example, agar, calcium carbonate, potato starch or cassava starch, alginic acid, some composite silicate and sodium carbonate; (e) slow-dissolving agents, for example, wax, (f) sorbefacients, for example, quaternary ammonium compounds; (g) wetting agents, for example, cetyl alcohol and glycerin monostearate; (h) adsorbents, for example, kaolin; and (i) lubricants, for example, talc, calcium stearate, magnesium stearate, solid polyethylene glycol, sodium dodecyl sulfate or mixture thereof. Dosage forms such as capsules, tablets and pills may further include bufferings.

Solid dosage forms, such as tablets, rotulas, capsules, pills and granules, can be prepared with coatings or shells such as enteric coatings or other materials known by those skilled in the art. They can include opaque agent. Furthermore, active compounds or compounds in the composition can be slow-released in a part of alimentary canal. Examples of embedding components include polymer substances and wax substances. If necessary, the active compounds also can be combined with one or more of excipients mentioned above to make a form of micro-capsule.

Liquid dosage forms for oral administration include pharmaceutically acceptable emulsions, solutions, suspensions, syrups or tinctures. Besides active compounds, the liquid dosage forms may include inert diluents conventionally used in this field, such as water or other solvents, solubilizing agents and emulsifying agents, such as ethanol, isopropanol, ethyl carbonate, ethyl acetate, propylene glycol, 1,3-butanediol, dimethylformamide and oil, particularly cottonseed oil, peanut oil, corn germ oil, olive oil, caster oil and sesame oil or mixtures of these substances.

Besides the inert diluents, the composition may also include auxiliary agents such as wetting agents, emulsifying agents and suspending agents, sweetening agents, corrigents and flavors.

Besides the active compounds, the suspensions may include suspending agents, for example, ethoxylated isooctadecanol, polyoxyethylene sorbitol, and dehydrated sorbate, microcrystalline cellulose, methanol aluminium and agar or mixtures of these substances.

Compositions for parenteral injection may include physiologically acceptable sterile solutions, dispersions, suspensions or emulsions with or without water, and sterile powders for being redissolved to form sterile injection solutions or dispersions. Appropriate carriers, diluents, solvents or excipients with or without water include water, ethanol, polyalcohols and appropriate mixtures thereof.

Dosage forms of the compounds of the present invention for local administration include ointments, powders, plasters, sprays and inhalants. The active component is mixed with physiologically acceptable carriers and any antiseptics, buffers, or propellants if necessary under sterile condition.

The compounds of the present invention can be administered alone or in combination with other pharmaceutically acceptable compounds.

When used as a pharmaceutical composition, the compounds of the present invention is applied in a secure and effective dosage to mammalians, such as human. The applied dosage is a pharmaceutically effective dosage for administration. Taking a person with weight of 60 kg for example, the daily dose is usually 1~1000 mg, preferably 20~500 mg. The specific dosage certainly should be considered according to the factors, such as routes of administration and health condition of patients, all of which belong to the conventional skills for proficient physicians.

The present invention has the following advantages:
(a) The salts of the present invention have good solubility in conventional solvents, such as water and methanol, and are suitable for conventional preparations.
(b) The salts of the present invention are proved to have good bioavailability in animal body.

Therefore, the compounds of the present invention are applicable to be developed as an excellent antihypertensive drug to be applied in clinic.

The present invention is further illustrated by the following examples. It should be understood that these examples are illustrative only and will not intend to limit the scope of the invention. The experimental methods which have not be noted any specific conditions are generally according to conventional conditions, or according to the suggested conditions suggested by manufacturers. Unless otherwise indicated, the parts and percents are both by weight.

Example 1

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester (compound 1)

2-butyl-4-chloro-1-[2'-(1H-tetrazol-5-yl)1,1'-biphenyl-methyl]imidazole-5-carboxylic acid (prepared by the method disclosed in U.S. Pat. No. 5,138,069) was reacted with trityl chloride to obtain 2-butyl-4-chloro-1-[2'-(1-triphenylmethyl-tetrazol-5-yl)1,1'-biphenyl-methyl]imidazole-5-carboxylic acid. To a 100 ml of one-necked flask, 0.523 g of 2-butyl-4-chloro-1-[2'-(1-triphenylmethyl-tetrazol-5-yl)1,1'-biphenyl-methyl]imidazole-5-carboxylic acid, 0.124 g of potassium carbonate, and 5 ml of N,N-dimethylacetamide were added in turn. The solution was stirred at the room temperature for 20 minutes. Then 0.562 g of 1-chloromethyl isopropyl carbonate was added and the mixture was reacted at 45-50° C. for 16 h. After the reaction was completed, the mixture solution was filtered, and 30 ml of water was added into the filtrate. The resulting mixture was extracted with 30 ml of ethyl acetate twice. The organic phase was dried and concentrated to give 1.724 g of oil, which was directly used in the next reaction without purification.

10 ml of dioxane and 5 ml of 4 mol/L HCl were added, and the resulting mixture was reacted at the room temperature for 16 h. After the reaction was completed, the solution was adjusted to pH 6-7 using aqueous sodium bicarbonate solution. The solution became turbid, and was extracted with ethyl acetate. The organic phase was washed with saturated brine, dried, concentrated to give 0.436 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester.

$^1$H-NMR: (CDCl$_3$)

$\delta_H$(ppm): 0.89 (t, 3H, J=14.6), 1.24 (d, 6H, J=6.3), 1.37 (m, 2H, J=22.1), 1.69 (m, 2H, J=30.5), 2.64 (t, 2H, J=15.5), 4.81 (m, 1H, J=12.4), 5.54 (s, 2H), 5.86 (s, 2H), 6.95-7.64 (8H), 8.08 (d, 1H, J=7.42)

ESI (+) m/z: 552.7

Mp: 134.5-136° C.

Example 2

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt (compound 2)

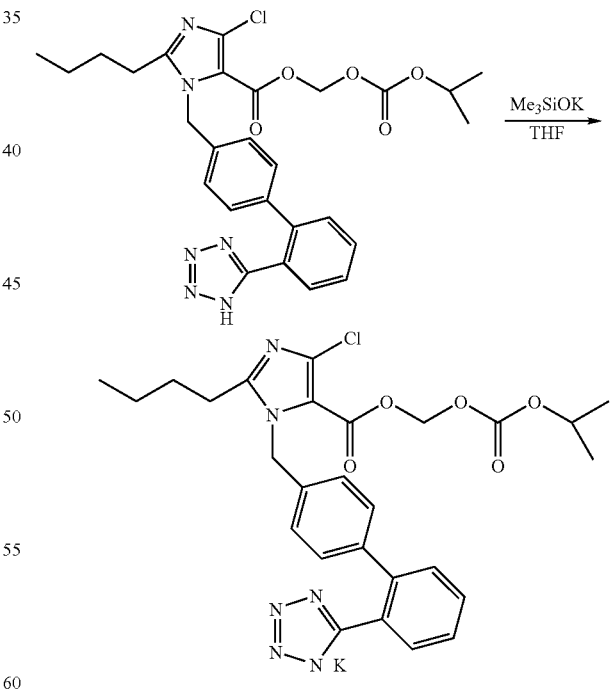

To a 100 ml of three-necked flask, 2.50 g (4.52 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester and 25 ml of tetrahydrofuran (THF) were added. The solution was stirred to be dissolved. Then 0.645 g (4.52 mmol) of, trimethyl silanol potassium (content 90%, Aldrich INC.) dissolved in 15 ml of THF were added and the mixture was reacted at 28° C. for 17 h.

The reaction was completed and a small quantity of white flocs existed in the solution, which was separated by filtration. The filtrate was concentrated in vacuo to give a crude white solid which undergo a recrystallization with a mixed solution of isopropyl ether and ethanol (3:1 v/v) to give 1.42 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt with a yield of 53%.

Mp: 189.5~189.7° C.

Element analysis:

| $C_{27}H_{28}ClKN_6O_5$ | | |
|---|---|---|
| items | Measured value % | Calculated value % |
| C | 54.76 | 54.81 |
| H | 4.75 | 4.74 |
| N | 14.20 | 14.21 |

| IR (KBr) | | | |
|---|---|---|---|
| Absorption peaks (cm$^{-1}$) | Vibration types | groups | Absorption peaks intensity |
| 3050 | $\gamma_{C-H}$ | Ar—H | w |
| near 2980 | $\gamma_{C-H}$ | CH3, CH2 | m |
| 2800 | $\gamma_{C-H}$ | O-CH-O | w |
| 1757, 1716 | $\gamma_{C=O}$ | C=O | s |
| 1508 | $\gamma_{C=C(Ar)}$ | Ar | m |
| 1379, 1458 | $\delta_{asC-H}$ | CH3 | m |
| 823 | $\delta_{asC-H(Ar)}$ | Ar—H (p-disubstituted) | m |
| 740 | $\delta_{asC-H(Ar)}$ | Ar—H (o-disubstituted) | m |

$^1$H-NMR: (CD$_3$OD)

$\delta_H$ (ppm): 0.87 (t, 3H, J=14.3), 1.274 (d, 6H, J=6.2), 1.31 (m, 2H, J=22.22), 158 (m, 2H, J=15.6), 2.66 (t, 2H, J=15.4), 4.84 (m, 1H, J=8.8), 5.56 (s, 2H), 5.86 (s, 2H), 6.95-7.64 (8H)

+c-ESI m/z: 591.6 (M+1)

Example 3

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt (compound 2)

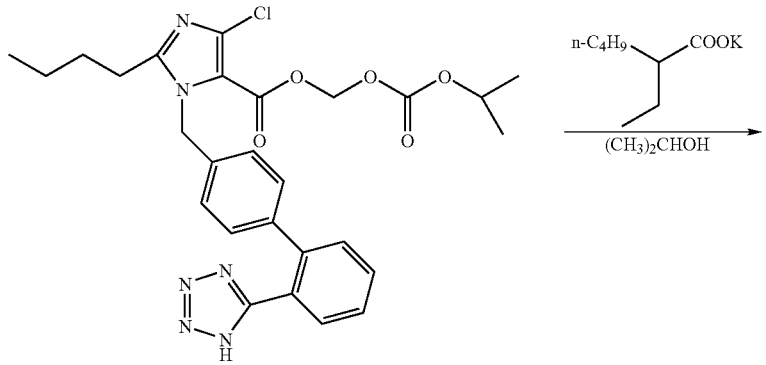

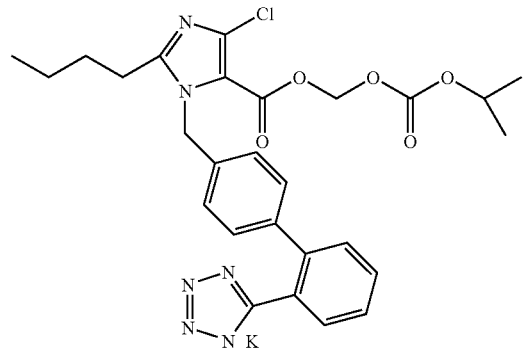

2.0 g (3.62 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester was dissolved in 20 ml of isopropanol. Then 4.83 g (3.98 mmol) of potassium 2-ethyl hexanate with a concentration of 15% was added slowly at the room temperature (25° C.). The mixture was heated to 75° C. and reacted for 17 h.

Stopped heating, the solution was cooled naturally to room temperature and standing for 48 h. A small quantity of white solid is precipitated, which was separated by filtration to obtain 0.51 g white solid with a yield of 24%, and after being purified to give 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt.

Example 4

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt (compound 2)

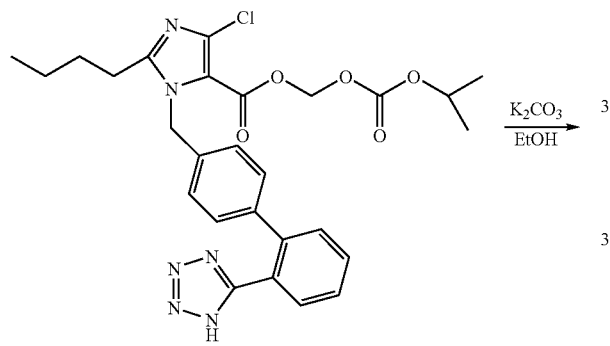

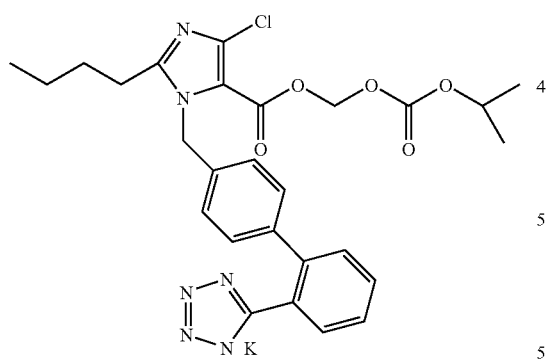

15 ml of anhydrous ethanol and 0.276 g (2 mmol) of potassium carbonate were added to 2.212 g (4 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester in turn. The mixture of solution were heated to 30° C., and reacted for 20 h. After the reaction was completed, the solution was filtered.

The filtrate was concentrated in vacuo to dry to give a white solid which undergo a recrystallization with ethanol-isopropyl ether to give 1.63 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt with a yield of 69%.

Example 5

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, sodium salt (compound 3)

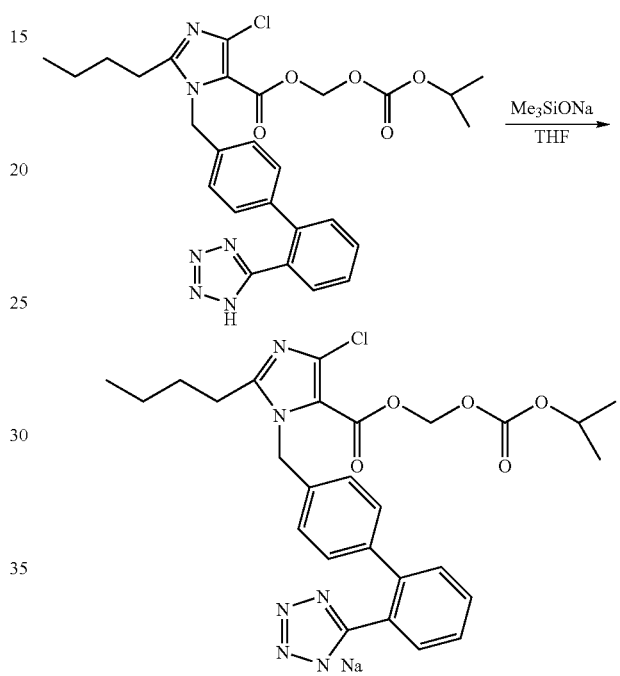

2.5 g (4.53 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester was dissolved in 15 ml of anhydrous THF dried by metallic sodium at the room temperature. 4.6 ml of 1.0 M trimethyl silanol sodium dichloromethane was added to the mixture and reacted for 24 h at the temperature of 25° C. The reaction solution was concentrated to ½ volume, standing for 48 h, and a white solid is precipitated. It was filtered to give 0.923 g of crude product with a yield of 35.5%, which undergo a recrystallization with a mixture of ethanol-isopropyl ether to obtain 0.563 g 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, sodium salt.

Mp: 93.0~96.8° C.

Element analysis:

| | $C_{27}H_{28}ClN_6NaO_5$ | |
|---|---|---|
| Items | Measured value % | Calculated value % |
| C | 56.44 | 56.40 |
| H | 4.90 | 4.91 |
| N | 14.60 | 14.62 |

| IR(KBr) | | | |
|---|---|---|---|
| Absorption peaks (cm$^{-1}$) | Vibration types | groups | Absorption peaks intensity |
| 3050 | $\gamma_{C-H}$ | Ar—H | w |
| near 2958 | $\gamma_{C-H}$ | CH$_3$, CH$_2$ | m |
| 2871 | $\gamma_{C-H}$ | O⌒O / H | w |
| 1759, 1732 | $\gamma_{C=O}$ | C=O | s |
| 1517 | $\gamma_{C=C(Ar)}$ | Ar C=C | m |
| 1383, 1458 | $\delta_{asC-H}$ | CH$_3$ | m |
| near 840 | $\delta_{asC-H(Ar)}$ | Ar—H (p-disubstituted) | m |
| 763 | $\delta_{asC-H(Ar)}$ | Ar—H (o-disubstituted) | m |

$^1$H-NMR: (CDCl$_3$)
$\delta_H$(ppm): 0.88 (t, 3H, J=14.7), 1.27 (d, 6H, J=6.2), 1.33 (m, 2H, J=15.4), 1.58 (m, 2H, J=30.5), 2.66 (t, 2H, J=15.4), 4.84 (m, 1H, J=4.01), 5.55 (s, 2H), 5.86 (s, 2H), 6.88-7.54 (8H)
+c-ESI m/z: 575.6 (M+1)

Example 6

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, sodium salt (compound 3)

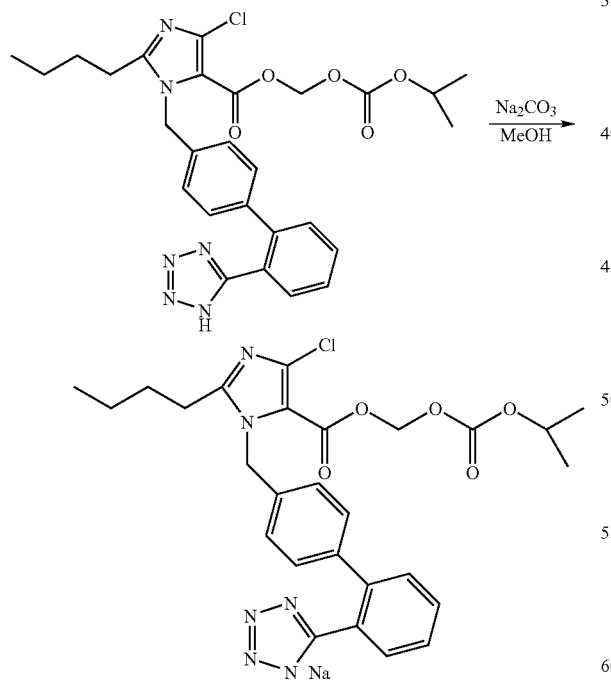

15 ml of anhydrous methanol and 0.212 g (2 mmol) of sodium carbonate were added into 2.212 g (4 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester in turn. The mixture were heated to 40° C., and reacted for 20 h. After the reaction was completed, the solution was filtered. The filtrate was concentrated in vacuo to be dry and give a white solid which undergo a recrystallization with a mixture of ethanol-isopropyl ether to obtain 1.40 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, sodium salt with a yield of 61%.

Example 7

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt (compound 4)

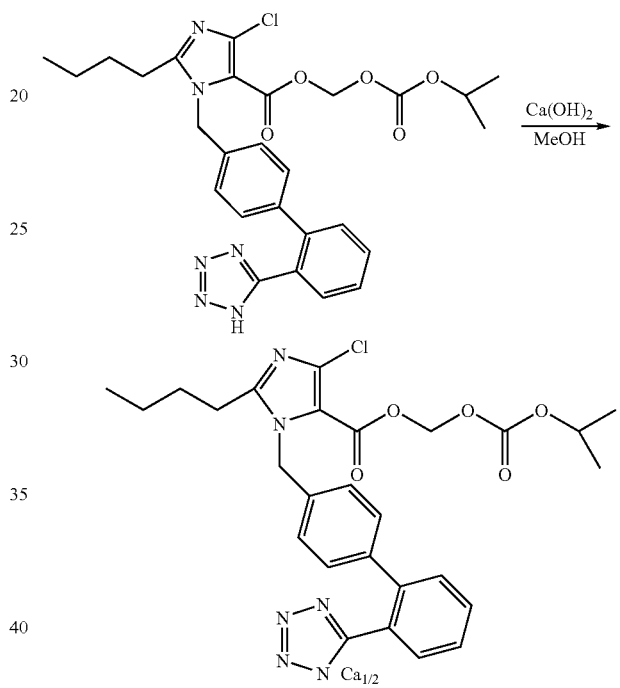

15 ml of anhydrous methanol and 0.148 g (2 mmol) of calcium hydroxide were added to 2.212 g (4 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester in turn. The mixture were heated to 30° C., and reacted for 20 h. After the reaction was completed, the solution was filtered. The filtrate was concentrated in vacuo to be dry and give a white solid which undergo a recrystallization by a mixture of acetone-isopropyl ether to obtain 1.77 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt with a yield of 77.1%.
Mp: 156.2~156.7° C.
Element analysis:

| $C_{54}H_{58}CaCl_2N_{12}O_{10}$ | | |
|---|---|---|
| Items | Measured value % | Calculated value % |
| C | 56.60 | 56.64 |
| H | 5.10 | 5.07 |
| N | 14.66 | 14.68 |

| IR(KBr) | | | |
|---|---|---|---|
| Absorption peaks ($cm^{-1}$) | Vibration types | groups | Absorption peaks intensity |
| >3000, partially overlapped with the peak for $H_2O$ near 2960 | $\gamma_{C-H}$ | Ar—H | w |
| | $\gamma_{C-H}$ | $CH_3$, $CH_2$ | m |
| 2880 | $\gamma_{C-H}$ | O-CH-O | w |
| 1761, 1716 | $\gamma_{C=O}$ | C=O | s |
| 1508 | $\gamma_{C=C(Ar)}$ | Ar C=C | m |
| 1379, 1458 | $\delta_{asC-H}$ | $CH_3$ | m |
| near 850 | $\delta_{asC-H(Ar)}$ | Ar—H (p-disubstituted) | m |
| 761 | $\delta_{asC-H(Ar)}$ | Ar—H (o-disubstituted) | m |

$^1$H-NMR: (DMSO-d6)
$\delta_H$(ppm): 0.82 (t, 3H, J=14.6), 1.22 (d, 6H, J=6.2), 1.27 (m, 2H, J=37.7), 1.54 (m, 2H, J=15.4), 2.64 (t, 2H, J=15.4), 4.80 (m, 1H, J=12.5), 5.53 (s, 2H), 5.84 (s, 2H), 6.95-7.64 (8H)
+c-ESI m/z: 553.3 (M–19)

Example 8

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt (compound 4)

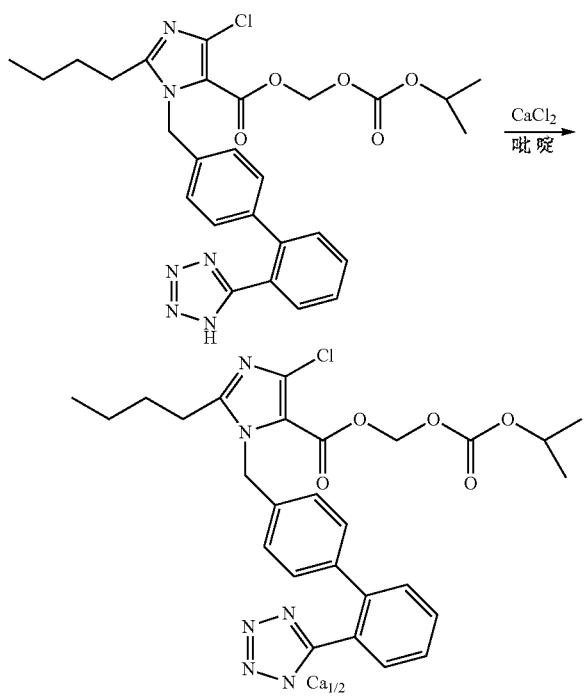

25 ml of anhydrous methanol, 0.222 g (2 mmol) of anhydrous calcium chloride and 0.36 g (4.5 mmol) of pyridine were added to 2.212 g of (4 mmol) 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester in turn. The mixture was heated to 30° C., and reacted for 17 h. After the reaction was completed, the solution was filtered. The filtrate was concentrated in vacuo to dry to give a white solid which undergo a recrystallization with a mixture of ethanol-isopropyl ether to obtain 1.01 g of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt with a yield of 44.0%.

Example 9

2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt (compound 4)

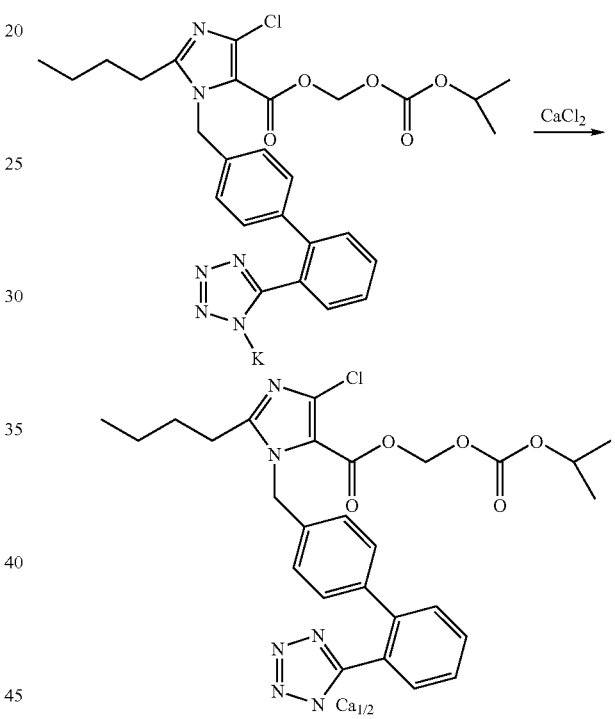

591 mg (1 mmol) of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, potassium salt was dissolved in 5 ml of water. Then aqueous solution of $CaCl_2$ (122 mg dissolved in 2 ml water) was slowly added thereto at the room temperature and the solution became white turbid. The mixture was stirred for 2 h, and concentrated in vacuo to yield a white solid. It underwent a recrystallization with a mixture of ethanol-isopropyl ether to obtain 257 mg of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, calcium salt as a white solid product with a yield of 45%.

Example 10

Solubility Test

Each compound prepared above was weighted and added to solvents with different volume capacity. The solution was stirred strongly for 30 seconds in each 5 minutes and the solubility condition was observed within 30 minutes. The solubility was described as follows:

Easily soluble: 1 g of compound can be dissolved in 1 ml~10 ml solvent;
Soluble: 1 g of compound can be dissolved in 10 ml~30 ml solvent;
A little soluble: 1 g of compound can be dissolved in 30 ml~100 ml solvent;
Slightly soluble: 1 g of compound can be dissolved in 100 ml~1000 ml solvent;

| Compounds | Solubility (in $H_2O$) | Solubility (in methanol) |
|---|---|---|
| Compound 1 | Slightly soluble | Slightly soluble |
| Compound 2 | Easily soluble | Easily soluble |
| Compound 3 | Easily soluble | Easily soluble |
| Compound 4 | Easily soluble | Easily soluble |

Example 11

Metabolism Conversion of the Compounds in vivo

SD rats are orally administrated by intragastric infusion with a dosage of 20 mg/kg of each compound. Blood samples are collected from orbits at different times after the administration. Having been pre-treated, the blood samples are analyzed by using HPLC method to determine the amount of original type of each compound in the blood plasma. The following results have been obtained: The original type of each compound can not be detected in blood, but the blood drug level of 2-butyl-4-chloro-1-[2'-(1H-tetrazol-5-yl)1,1'-biphenyl-methyl]imidazole-5-carboxylic acid (shortly named EXP3174) is gradually increasing. According to the structural characteristic of each compound, it is understood that each compound was converted quickly to EXP3174 in vivo. Therefore, EXP3174 is used to be an index of absorption in vivo for each compound.

Example 12

SD Rats Drug Absorption Test

Rats intravenous administration: healthy SD rats were intravenous injected at the tails by EXP3174 (the volume of administration is 10 ml/kg) with a dosage of 7.9 mg/kg. The intravenous blood was collected from venous plexus behind eyeballs of rats at different time before and after administration, and the blood plasma is prepared by separated. The concentration of EXP3174 in blood plasma was measured by liquid chromatography-tandem mass spectrometry. The pharmacokinetic parameters of EXP3174 were calculated according to the drug concentration-time curve.

Rat intragastric infusion: Healthy SD rats are orally administrated each compound by intragastric infusion with the same dosage as EXP3174. Blood samples are collected from an orbit at different time after the administration. The blood plasma is prepared by separated and analyzed by liquid chromatography-tandem mass spectrometry to determine the concentration of the active metabolite, EXP3174, in the blood plasma. The pharmacokinetic parameters of EXP3174 were calculated according to the drug concentration-time curve.

According to the rat test mentioned above, $T_{max}$ and bioavailability of the compounds are obtained as follows:

| Compound | $T_{max}$ | Bioavailability |
|---|---|---|
| Compound 1 | 2 h | 4.11% |
| Compound 2 | 0.5 h | 26.7% |
| Compound 3 | 0.5 h | 22.6% |
| Compound 4 | 0.5 h | 21.3% |

Example 13

Pharmaceutical Composition

| Compound 2 | 23 g |
|---|---|
| Starch | 140 g |
| Microcrystalline cellulose | 67 g |

According to conventional methods, the substances mentioned above are mixed to be homogeneous, and then put into common gelatine capsules to obtain 1000 capsules.

The capsules containing compounds 3 and 4 are prepared respectively according to the similar method.

All documents cited herein are incorporated into the present invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

The invention claimed is:

1. A pharmaceutically acceptable salt of formula (I)

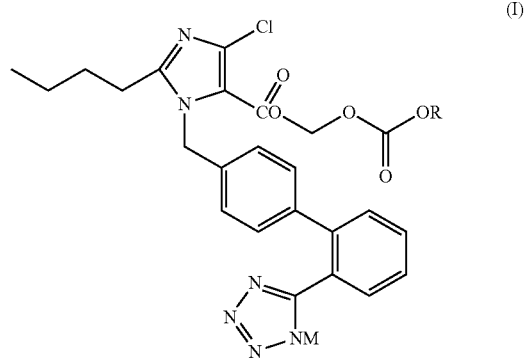

wherein R is selected from the group consisting of hydrogen, straight or branched $C_1$-$C_4$ alkyl, or $C_3$-$C_7$ cycloalkyl, wherein said alkyl or cycloalkyl group is unsubstituted or substituted by 1-3 substituents selected from the group consisting of F, Cl, Br, and OH;

M is metal ion or ammonium ion, where the metal ion is potassium, sodium, or calcium.

2. The salt according to claim 1, wherein R is selected from the group consisting of straight or branched $C_2$-$C_4$ alkyl.

3. The salt according to claim 1, wherein R is selected from the group consisting of ethyl, isopropyl or tertiary butyl.

4. The salt according to claim 1, wherein R is isopropyl.

5. The salt according to claim 1, wherein the salt is a potassium salt, sodium salt or calcium salt.

6. A method for preparing a pharmaceutically acceptable salt of formula (I) as in claim 1 comprising the following steps:

(a) reacting, in an inert organic solvent, a compound of formula (II) with reagents which can provide a metal ion or ammonium ion to form a salt of formula (I),

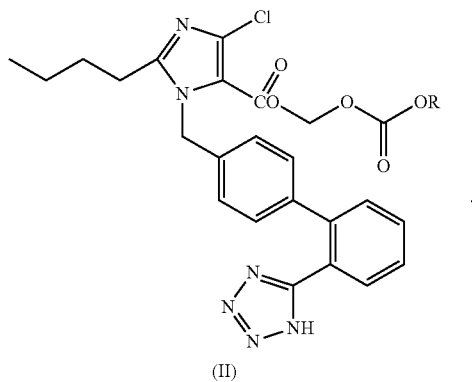

(II)

→

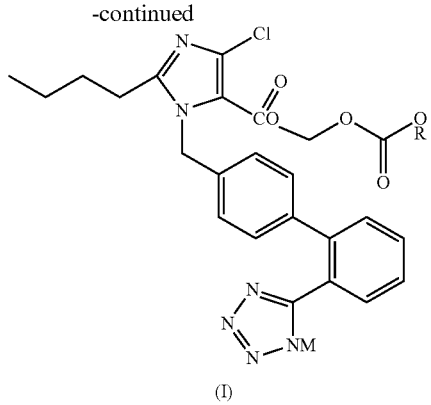

(I)

wherein R is selected from the group consisting of hydrogen, straight or branched $C_1$-$C_4$ alkyl, or $C_3$-$C_7$ cycloalkyl, wherein alkyl or the cycloalkyl group is unsubstituted or substituted by 1-3 substituents selected from the group consisting of F, Cl, Br, and OH, M is a metal ion or ammonium ion, where the metal ion is potassium, sodium, or calcium; and (b) isolating the salt of formula (I) from a mixture of the reaction in (a).

7. A pharmaceutical composition comprising the pharmaceutically acceptable salt according to claim 1 and a pharmaceutically acceptable carrier.

\* \* \* \* \*